(12) United States Patent
Johnson et al.

(10) Patent No.: US 8,319,004 B2
(45) Date of Patent: Nov. 27, 2012

(54) TRAINING ARTICLE FOR DELIVERING UNIQUE SENSATIONS

(75) Inventors: Eric D. Johnson, Larsen, WI (US); Jason C. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1814 days.

(21) Appl. No.: 11/506,356

(22) Filed: Aug. 17, 2006

(65) Prior Publication Data

US 2008/0045913 A1  Feb. 21, 2008

(51) Int. Cl.
*A61F 13/15* (2006.01)

(52) U.S. Cl. ........ 604/361; 604/362; 604/366; 604/367; 604/364

(58) Field of Classification Search .................. 604/361, 604/362, 366, 367, 364
See application file for complete search history.

(56) References Cited

U.S. PATENT DOCUMENTS

| | | |
|---|---|---|
| 2,602,302 A | 7/1952 | Poux |
| 3,132,688 A | 5/1964 | Nowak |
| 3,175,558 A | 3/1965 | Caillonette et al. |
| 3,900,035 A | 8/1975 | Welch et al. |
| 4,462,224 A | 7/1984 | Dunshee et al. |
| 4,585,002 A | 4/1986 | Kissin |
| 4,596,250 A | 6/1986 | Beisang, III et al. |
| 4,704,116 A | 11/1987 | Enloe |
| 4,781,193 A | 11/1988 | Pagden |
| 4,798,603 A | 1/1989 | Meyer et al. |
| 4,860,748 A | 8/1989 | Chiurco et al. |
| 4,886,063 A | 12/1989 | Crews |
| 4,940,464 A | 7/1990 | Van Gompel et al. |
| 4,981,135 A | 1/1991 | Hardy |
| 5,167,655 A | 12/1992 | McCoy |
| 5,176,672 A | 1/1993 | Bruemmer et al. |
| 5,266,592 A | 11/1993 | Grub et al. |
| 5,348,750 A | 9/1994 | Greenberg |
| 5,415,624 A | 5/1995 | Williams |
| 5,486,166 A | 1/1996 | Bishop et al. |
| 5,490,846 A | 2/1996 | Ellis et al. |
| 5,509,915 A | 4/1996 | Hanson et al. |

(Continued)

FOREIGN PATENT DOCUMENTS

EP  1 263 379 B1  10/2004

(Continued)

OTHER PUBLICATIONS

Bouhassira, Didier et al., "Investigation of the Paradoxical Painful Sensation ('Illusion of Pain') Produced by a Thermal Grill," *Pain*, International Association for the Study of Pain, published by Elsevier, vol. 114, 2005, pp. 160-167.

(Continued)

*Primary Examiner* — Jacqueline F. Stephens
(74) *Attorney, Agent, or Firm* — Randall W. Fieldhack

(57) ABSTRACT

An aid is usable with a wearer's garment, the aid including a structural layer having a skin-facing side, wherein the structural layer is adapted to be positioned within the garment such that the skin-facing side is in at least partial skin contact with the wearer; and a thermal grill disposed on the structural layer. Also, an absorbent article delivers discomfort without causing physiological damage, the article including a bodyside liner; a plurality of warm portions disposed on the bodyside liner; and a plurality of cool portions disposed on the bodyside liner, wherein the warm portions and cool portions are disposed in an alternating pattern.

43 Claims, 2 Drawing Sheets

U.S. PATENT DOCUMENTS

| | | |
|---|---|---|
| 5,545,197 A | 8/1996 | Bowen |
| 5,628,769 A | 5/1997 | Saringer |
| 5,649,914 A | 7/1997 | Glaug et al. |
| 5,702,376 A | 12/1997 | Glaug et al. |
| 5,766,389 A | 6/1998 | Brandon et al. |
| 5,785,980 A | 7/1998 | Mathewson |
| 5,792,213 A | 8/1998 | Bowen |
| 5,797,892 A | 8/1998 | Glaug et al. |
| 5,820,973 A | 10/1998 | Dodge, II et al. |
| 5,993,433 A | 11/1999 | St. Louis et al. |
| 6,096,067 A | 8/2000 | Cramer et al. |
| 6,248,097 B1 | 6/2001 | Beitz et al. |
| 6,248,125 B1 | 6/2001 | Helming |
| 6,308,341 B1 | 10/2001 | Shelton |
| 6,567,696 B2 | 5/2003 | Voznesensky et al. |
| 6,642,427 B2 * | 11/2003 | Roe et al. .................. 604/361 |
| 6,645,190 B1 | 11/2003 | Olson et al. |
| 6,648,909 B2 | 11/2003 | Helming |
| 6,658,432 B1 | 12/2003 | Alavi et al. |
| 6,770,064 B1 | 8/2004 | Ruscher |
| 6,791,004 B2 | 9/2004 | Sprengard Eichel et al. |
| 6,869,441 B2 | 3/2005 | Agarwal et al. |
| 6,881,219 B1 | 4/2005 | Agarwal et al. |
| 7,083,839 B2 | 8/2006 | Fish et al. |
| 2002/0169427 A1 | 11/2002 | Roe et al. |
| 2004/0127880 A1 | 7/2004 | Weber |
| 2004/0254550 A1 | 12/2004 | Huang et al. |
| 2007/0049881 A1 | 3/2007 | Ales, III et al. |
| 2007/0142797 A1 | 6/2007 | Long et al. |
| 2007/0252712 A1 | 11/2007 | Allen et al. |

FOREIGN PATENT DOCUMENTS

| | | |
|---|---|---|
| WO | WO 96/19172 A1 | 6/1996 |
| WO | WO 00/37009 A2 | 6/2000 |
| WO | WO 01/10366 A1 | 2/2001 |
| WO | WO 01/26499 A1 | 4/2001 |
| WO | WO 01/26527 A1 | 4/2001 |
| WO | WO 01/26528 A1 | 4/2001 |
| WO | WO 01/26530 A1 | 4/2001 |
| WO | WO 01/27239 A1 | 4/2001 |
| WO | WO 02/064069 A2 | 8/2002 |
| WO | WO 03/094644 A1 | 11/2003 |
| WO | WO 2004/043311 A1 | 5/2004 |
| WO | WO 2004/084782 A1 | 10/2004 |
| WO | WO 2005/018514 A1 | 3/2005 |

OTHER PUBLICATIONS

Craig, A.D. and M.C. Bushnell, "The Thermal Grill Illusion: Unmasking the Burn of Cold Pain," *Science*, vol. 265, Jul. 8, 1994, pp. 252-255.

Blouin, Jean-Sebastian et al., "Postural Stability is Altered by the Stimulation of Pain But Not Warm Receptors in Humans," *BMC Musculoskeletal Disorders*, vol. 4, No. 1, BioMed Central, London, GB, Oct. 17, 2003, pp. 1-9.

* cited by examiner

TRAINING ARTICLE FOR DELIVERING UNIQUE SENSATIONS

FIELD

Some aspects of the invention relate to a system for delivering unique sensations for training purposes, and in particular to a system for delivering a unique sensation for training purposes without causing physiological damage.

BACKGROUND

An uncomfortable sensation of heat is elicited within an individual when the individual touches interlaced warm and cool bars with their skin. The sensations of discomfort and temperature and even pain have been analogized to the burning sensation that accompanies touching extremely cold objects.

One of the prevailing explanations of this burning sensation is that the perception of "heat" is a fusion of sensations resulting from simultaneous activation of warm and cool sensors within the body. Modern physiological findings have confirmed the existence of separate cutaneous receptors for warm and cool. It is interesting to note that the cutaneous receptors that are associated with a cold sensation appear to be activated by low and high temperatures.

A thermal grill is a device that includes interlaced or alternating warm and cool portions that are able to cause discomfort and even pain to an individual without causing physiological damage when the individual touches the interlaced warm and cool portions. The relative size, shape, design, configuration, temperature, and orientation of the interlaced warm and cool portions may be varied to adjust the level of discomfort that can be generated within an individual that touches the thermal grill with their skin.

Many articles intended for personal wear, e.g., such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged wetness exposure. In some instances, such as for toilet training children, there is a belief that children must be given a signal such as an uncomfortable and/or wet feeling against the skin to facilitate toilet training by making the child more aware that the act of urination has occurred. On the other hand, there is a counter-balancing concern about the possibility of skin irritations and rashes caused by prolonged wetness against the skin if the articles are less absorbent to allow the child to sense wetness. However, by making articles such as training pants so absorbent, it is difficult for the wearer to realize that an insult of the article has occurred.

To this end, some articles intended for personal wear during toilet training include means for alerting a child to urination without leaving a substantial amount of wetness against the skin. For example, one such article includes a temperature changing element that allows the wearer to feel a change in temperature against the skin upon urination, thereby alerting the wearer to the urination.

Another example of training pants intended to provide a sensory indication of urination includes an element that changes size after urination, e.g., expanding toward the wearer's crotch region. However, such elements are typically surrounded by highly absorbent structures (sometimes referred to as absorbent cores) which compete for and may draw urine away from the element, thereby prolonging or otherwise inhibiting the expansion thereof and diminishing its potential training effectiveness. Also, superabsorbent material (SAM) which is used to make the highly absorbent structures of such articles expands upon absorbing urine. Such expansion may mask or otherwise cushion the feeling of the expanded sensory element, thus making it difficult for the wearer to sense the intended signal.

Another example of training pants intended to provide a sensory indication of urination includes an element that completes a circuit and broadcasts an audible or visual alarm, alerting a caregiver that an insult has occurred.

Consequently, while there has been progress in the design of personal wear articles capable of alerting a wearer to a release of liquid body exudates, there continues to be a need for improvements in such articles.

SUMMARY OF THE INVENTION

The present invention relates to a training system for delivering a unique sensation without causing physiological damage. The training system includes a thermal grill that may be used to deliver a unique sensation to an individual without causing physiological damage when the individual activates the thermal grill.

In one aspect, the system includes a thermal grill that causes a unique sensation to an individual without physiologically damaging the individual when the individual activates the thermal grill.

More specifically, the present invention includes an aid for use with a wearer's garment, the aid including a structural layer having a skin-facing side, wherein the structural layer is adapted to be positioned within the garment such that the skin-facing side is in at least partial skin contact with the wearer; and a thermal grill disposed on the structural layer.

In addition, the present invention includes an absorbent article for delivering a unique sensation without causing physiological damage, the article including a bodyside liner; a plurality of warm portions disposed on the bodyside liner; and a plurality of cool portions disposed on the bodyside liner, wherein the warm portions and cool portions are disposed in an alternating pattern.

Also, the present invention includes an absorbent article for delivering a unique sensation without causing physiological damage, the article including a structural layer, wherein the structural layer is one of a bodyside liner, a surge layer, an absorbent layer, and an outer cover; and a thermal grill disposed on the structural layer.

In addition, the present invention includes a system of aids for use with a wearer's garment, the system including a first structural layer having a first thermal grill with first warm and cool portions, the first thermal grill exhibiting a first temperature difference between the first warm and cool portions when activated; and a second structural layer having a second thermal grill with second warm and cool portions, the second thermal grill exhibiting a second temperature difference between the second warm and cool portions when activated; wherein the second temperature difference is greater than the first temperature difference.

Also, the present invention includes a method for providing a system of aids, the method including providing a first structural layer having a first thermal grill exhibiting a first level of discomfort when activated; and providing a second structural layer having a second thermal grill exhibiting a second level of discomfort when activated, wherein the second level of discomfort is greater than the first level of discomfort.

The purposes and features of the present invention will be set forth in the description that follows. Additional features of the invention may be realized and attained by the product and processes particularly pointed out in the written description and claims hereof, as well as from the appended drawings.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

Figure 1:
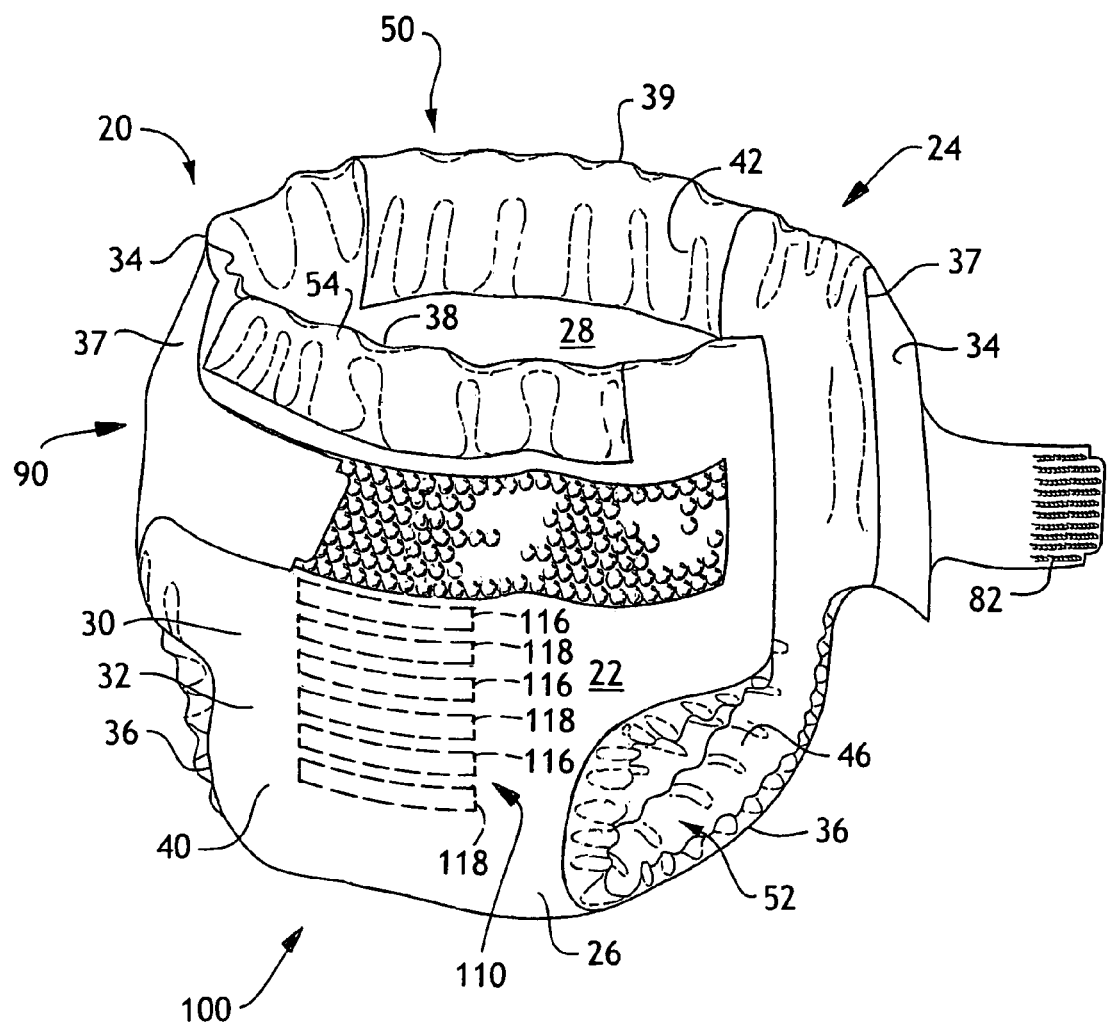
FIG. 1 illustrates a perspective view of a training article for delivering a unique sensation without causing physiological damage.

Repeat use of reference characters in the present specification and drawings is intended to represent the same or analogous features or elements of the present invention. The drawings are representational and are not necessarily drawn to scale. Certain proportions thereof may be exaggerated, while others may be minimized.

DETAILED DESCRIPTION OF THE INVENTION

The following detailed description references the accompanying drawings that show some example aspects of the invention. These example aspects are described in sufficient detail to enable those skilled in the art to practice the invention. It is to be understood that other aspects may be utilized, or structural changes made, such that the detailed description should not be considered as limiting the scope of the claims.

As used herein, a "thermal grill" is a device that includes interlaced warm and cool portions, where the temperature difference between the interlaced warm and cool portions causes an individual to feel discomfort (or pain) when the individual touches the thermal grill but does not cause physiological damage to the individual (the "thermal grill effect"). It should be noted that not causing physiological damage means that the stimuli that is provided by the thermal grill can not cause injury to an individual that touches the thermal grill with their skin. As used herein, "discomfort" means discomfort, pain, and/or an unpleasant, unique, unusual, hot, cold, or confusing feeling.

The interlaced warm and cool portions may be a variety of sizes, designs, configurations, shapes, temperatures, and orientations as long as the thermal grill generates discomfort within an individual without physiologically damaging the individual when the individual touches the thermal grill. The relative size and shape of the interlaced warm and cool portions that form the thermal grill will depend on the applications where the thermal grill is used.

Referring to FIG. 1, for non-limiting exemplary purposes, a training absorbent article 20 is shown. The training absorbent article 20 may or may not be disposable. It is understood that the present invention is suitable for use with various other training absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing training absorbent articles such as the training absorbent article 20 of the various aspects of the present invention are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., PCT Patent Application No. WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

A training absorbent article 20 is representatively illustrated in FIG. 1 in a partially fastened condition.

The training absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The training absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the training absorbent article 20, which when worn, wholly or partially cover or encircle the waist or mid-lower torso of the wearer. The crotch region 26 generally is that portion of the training absorbent article 20 which, when worn, is positioned between the legs of the wearer and covers the lower torso and crotch of the wearer. The training absorbent article 20 has a pair of laterally opposite side edges 36 and a pair of longitudinally opposite waist edges, respectively designated front waist edge 38 and back waist edge 39.

The illustrated training absorbent article 20 includes a chassis 32 that, in this aspect of the present invention, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The liner 42 can be generally adapted, i.e., positioned relative to the other components of the article 20, to be disposed toward the wearer's skin during wear of the training absorbent article. The chassis 32 may further include an absorbent structure (not shown) disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training absorbent article 20 may also suitably include leg elastic members (not shown), as are known to those skilled in the art.

In some aspects of the present invention, the training absorbent article 20 may further include a surge management layer (not shown) that may be optionally located adjacent the absorbent structure (not shown) and attached to various components in the article 20 such as the absorbent structure or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166 and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 1, the training absorbent article 20 further includes a pair of opposing elastic side panels 34 that are attached to the back region of the chassis 32. As shown particularly in FIG. 1, the side panels 34 may be stretched around the waist and/or hips of a wearer to secure the garment in place. The elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques. Ultimately, the side panels 34 are generally aligned with a waist region 90 of the chassis.

In an alternative aspect of the present invention, the elastic side panels may also be integrally formed with the chassis 32. For instance, the side panels 34 may comprise an extension of the bodyside liner 42, of the outer cover 40, or of both the bodyside liner 42 and the outer cover 40.

The side panels 34 are connected to the back region of the training absorbent article 20 and extend over the front region of the article when securing the article in place on a user. It should be understood, however, that the side panels 34 may alternatively be connected to the front region of the article 20 and extend over the back region when the article is donned.

With the training absorbent article 20 in the fastened position as partially illustrated in FIG. 1, the elastic side panels 34 may be connected by a fastening system 82 to define a 3-dimensional training absorbent article configuration having a waist opening 50 and a pair of leg openings 52. The waist opening 50 of the article 20 is defined by the waist edges 38 and 39 that encircle the waist of the wearer.

In the aspects of the present invention shown in the figures, the side panels are releasably attachable to the front region 22 of the article 20 by the fastening system 82. It should be understood, however, that in other aspects of the present invention the side panels may be permanently joined to the chassis 32 at each end. The side panels may be permanently bonded together, for instance, when forming a training pant or absorbent swimwear.

The fastening system 82 may include laterally opposite first fastening components adapted for refastenable engagement to corresponding second fastening components. The fastening system 82 may include any refastenable fasteners suitable for training absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

Suitable fastening systems are also disclosed in the previously incorporated PCT Patent Application No. WO 00/37009 published Jun. 29, 2000 by A. Fletcher et al. and the previously incorporated U.S. Pat. No. 6,645,190 issued Nov. 11, 2003 to Olson et al.

In addition to possibly having elastic side panels, the training absorbent article 20 may include various waist elastic members for providing elasticity around the waist opening. For example, as shown in the figures, the training absorbent article 20 can include a front waist elastic member 54 and/or a back waist elastic member (not shown).

FIG. 1 illustrates an example system 100 for delivering a unique sensation without causing physiological damage. The system 100 includes a thermal grill 110 that can cause discomfort to an individual without physiologically damaging the individual when the individual touches the thermal grill 110. In one aspect of the present invention, the thermal grill 110 is maintained in at least partial skin contact with a wearer of the training absorbent article 20 due to the positioning of the thermal grill 110 on the bodyside liner 42. It should be noted that the thermal grill 110 may be any suitable type of thermal grill.

The thermal grill 110 is positioned such that the thermal grill 110 is substantially imperceptible to the wearer prior to the first insult of the training absorbent article 20 by liquid body exudates, e.g., in the case of training pants, urine. The thermal grill 110 is longitudinally positioned in the crotch region 26 of the training absorbent article 20 between the leg openings 52 (see FIG. 1) thereof. However, it is contemplated that the longitudinal position of the thermal grill 110 within the crotch region 26 may be dependent on whether the training absorbent article 20 is to be worn by a boy or a girl. For example, placement of the thermal grill 110 in a more forward location within the crotch region 26 may be appropriate for boys, while placement in a more central location within the crotch region may be more appropriate for girls. It is also understood that the thermal grill 110 may be positioned other than in the crotch region 26 without departing from the scope of the present invention, as long as the thermal grill 110 is suitably positioned so as to become wet and perceptible by a wearer upon insult of the training absorbent article 20 by liquid body exudates.

While a single thermal grill 110 is shown in the illustrated aspect, it is contemplated that additional thermal grills 110 may be used to further enhance the signal to the wearer. For example, additional thermal grills 110 may be necessary for larger or older children with larger legs for whom the discomfort provided by a single thermal grill 110 may be insufficient to alert the wearer to his or her urination. A pair of thermal grills 110 may also be used in a configuration wherein one thermal grill 110 is positioned longitudinally where it is more likely to become wet upon urination by boys and the other thermal grill 110 is positioned longitudinally where it is more likely to become wet upon urination by girls, thereby accounting for differences between the target wetting areas of boys and girls.

The thermal grill 110 is a device that has one or more warm portions 116 that are interlaced or alternated with one or more cool portions 118. When the thermal grill 110 is activated and an individual contacts the thermal grill 110, the temperature difference between the warm and cool portions 116, 118 of the thermal grill 110 causes the individual to feel discomfort without physiologically damaging the individual. The relative size, shape, design, configuration, temperature, and orientation of the interlaced warm and cool portions 116, 118 may be varied in order to adjust the level of discomfort that can be generated within an individual that touches the thermal grill 110 with their skin. In addition, the warm and cool portions 116, 118 may be positioned in a generally horizontal orientation as shown in FIG. 1, in a generally vertical orientation (not shown), or in any other suitable orientation.

As used herein, the term "warm portion" and its plural refer to the portion of the thermal grill that is exothermic or potentially exothermic. The "warm portion" may actually feel warm as it does upon activation, or the "warm portion" may be potentially warm or warmable as it is before activation in that it includes material that will give off heat upon activation. Likewise, as used herein, the term "cool portion" and its plural refer to the portion of the thermal grill that is endothermic or potentially endothermic. The "cool portion" may actually feel cool as it does upon activation, or the "cool portion" may be potentially cool or coolable as it is before activation in that it includes material that will absorb heat upon activation.

Without committing to a particular theory, it is generally the case that the greater the temperature difference between the warm and cool portions 116, 118, the greater the probability that the wearer will experience consequential discomfort. A temperature difference in the range of 5-10 degrees C. is where a discomfort response typically begins to be experienced. At higher temperature differences, the intensity of the discomfort response and the percent of wearers who will have a discomfort response increases (see Bouhassira, et al, "Investigation of the Paradoxical Painful Sensation ('Illusion of Pain') Produced by a Thermal Grill"—Pain 114 (2005) 160-167).

Similarly, the width and spacing of the warm and cool portions 116, 118 in the training absorbent article 20 may be varied to vary the discomfort response. One source points to a preferable arrangement of 1 cm alternating stripes with a spacing between stripes of 3 mm. (see Craig and Bushnell "The Thermal Grill Illusion: Unmasking the Burn of Cold Pain"—Science Vol. 265, 8 Jul. 1994).

In various aspects of the present invention, the ability to vary the thermal grill effect from heating to discomfort to pain has application in providing varying levels of training assistance. For example, one set of absorbent articles 20 or other products with thermal grills 110 exhibiting little discomfort may be provided for early toilet trainers, while another set of absorbent articles 20 with thermal grills 110 exhibiting higher levels of discomfort may be provided for stubborn or reluctant trainers.

Similarly, one absorbent article 20 or other product may be supplied with two or more thermal grills 110 of varying levels of discomfort. For example, a structural layer may have a first thermal grill with first warm and cool portions exhibiting a first temperature difference between the first warm and cool portions when activated. That structural layer may also have a second thermal grill with second warm and cool portions a second temperature difference between the second warm and cool portions when activated. In this aspect, the second temperature difference is greater than the first temperature difference, yielding a more intense unique sensation with the second setting. The first setting may be used upon a first insult, and the second setting may be used upon a second insult if no action is taken following the first insult.

In one aspect, the first thermal grill is positioned on the structural layer in a location most likely to receive an insult. The second thermal grill is positioned concentrically outward from the first thermal grill, allowing the second thermal grill to become activated given enough time for urine to migrate to the second thermal grill, particularly if the urine migration is driven by a second insult.

In another aspect, the first thermal grill is positioned on the structural layer in a location most likely to receive an insult. The second thermal grill is positioned on the same or different layer, and is protected from the insult, at least initially, by a flow-delaying layer, a layer that dissolves in liquid, by encapsulation, or by any suitable means for delaying contact of urine with the second thermal grill. The second thermal grill becomes activated given enough time for urine to migrate to the second thermal grill, particularly if the urine migration is driven by a second insult.

In one aspect of the present invention, the warm and cool portions 116, 118 of the thermal grill 110 are formed by applying alternating stripes of endothermic and exothermic materials to one of the structural layers of the training absorbent article 20 including the inner liner, the surge layer, the absorbent layer, or the outer cover. In various aspects of the present invention, the endothermic and exothermic materials may be applied to the structural layer by blending the endothermic and exothermic materials into a lotion which is then applied to one of the structural layers such as the inner liner. In another aspect of the present invention, the endothermic and exothermic materials may also be combined into a liquid concentrated solution and sprayed onto the structural layer. In still another aspect of the present invention, the endothermic and exothermic materials may be produced in crystalline form and sprinkled or otherwise applied to the structural layer, using a suitable adhesive if desired. In any of these aspects, the endothermic and exothermic materials may be applied in alternating stripes, a checkerboard pattern, a concentric pattern of aligned circles or other shapes, or any other suitable geometric or non-geometric pattern. Similarly, different warm and/or cool portions 116, 118 may be colored using inks, dyes, or any other suitable substance. Finally, the endothermic and/or exothermic materials may be combined with an additive such as clay to increase the duration of cooling/heating.

The endothermic and exothermic materials are suitably responsive to contact with an aqueous solution, such as urine, to either absorb or release heat. The mechanism by which these are accomplished may be the dissolution of the endothermic and exothermic materials in the aqueous solution, the swelling of the endothermic and exothermic materials in the aqueous solution, and/or the reaction of the endothermic and exothermic materials in the aqueous solution. In particular aspects, the endothermic and exothermic materials are suitably in the form of particles which have a substantial energy difference between a dissolved state and a crystalline state, so that energy in the form of heat is absorbed or released to the environment upon contact with an aqueous solution such as urine. In other aspects, the endothermic and exothermic materials release or absorb energy during swelling or reacting of the endothermic and exothermic materials with an aqueous solution such as urine.

While a wide variety of endothermic and exothermic materials may result in a temperature change in response to contact with an aqueous solution, the selection of a particular endothermic or exothermic material and the determination of the amount to be used is based at least in part on the desired temperature change to be experienced by the wearer. Endothermic and exothermic materials suitable for use in the training absorbent article 20 include those that dissolve in an aqueous solution. The solubility of such endothermic and exothermic materials are suitably in the range of about 0.1 to about 3 grams of water ($H_2O$) per gram of agent (g/g), and more particularly from about 0.1 to about 2 g/g.

In various aspects of the present invention, the cool portions 118 may be formed using suitable endothermic materials that absorb heat during dissolution upon contact with an aqueous solution including, without limitation, salt hydrates such as sodium acetate, sodium carbonate, sodium sulfate, sodium thiosulfate, and sodium phosphate; anhydrous salts, such as ammonium nitrate, potassium nitrate, ammonium chloride, potassium chloride, sodium bromide, magnesium sulfate, and sodium nitrate; organic compounds, such as urea and acetone; carbohydrates such as xylitol, dextrose, and other sugars; and any other suitable materials.

The endothermic material can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued to Greenberg, and U.S. Pat. No. 5,266,592 issued to Grub et al.

In various aspects of the present invention, the warm portions 116 may be formed using suitable exothermic materials that release heat during dissolution including, without limitation, metal-halogen compounds such as aluminum chloride, magnesium chloride, calcium chloride, and manganese iodide; salts such as aluminum sulfate and potassium aluminum sulfate; metal hydroxides such as calcium oxide, barium oxide, and phosphorous pentoxide; and any other suitable material.

The endothermic and exothermic materials may also, or may instead, include a material that absorbs or releases heat during swelling upon contact with aqueous solution. By way of illustration, one suitable material that releases heat during such swelling is a polymer such as lightly cross-linked partially neutralized polyacrylic acid. Alternatively, or additionally, the endothermic and exothermic materials may include a material that absorbs or releases heat upon reaction with an aqueous solution. Additional examples of suitable endothermic and exothermic materials are further described in co-assigned U.S. Pat. No. 5,702,376 entitled "Toilet Training Aid Providing A Temperature And Dimensional Change Sensation," issued to Glaug et al.

In another aspect of the present invention, the cool portion 118 of the thermal grill may be constructed as described above, while the portion of the thermal grill 110 typically occupied by warm portions 116 is left without added material. In this aspect, the wearer's urine, which is quite warm as it leaves the body, provides the exothermic material for the warm portions 116. Alternatively, the warm portions 116 of the thermal grill 110 may be replaced with an absorbent material to hold the warm urine in place such that it acts as the exothermic material in the warm portions 116.

In yet another aspect of the present invention, the endothermic and exothermic materials may be applied on separate structural layers of the training absorbent article 20. For example, the exothermic material can be applied to the liner, and the endothermic material can be applied to the surge layer or other layer immediately adjacent to the liner.

In still another aspect of the present invention, a covering layer of any suitable material may be interposed between part or all of the thermal grill 110 and the skin of the wearer if skin contact with the thermal grill 110 is desired to be limited. Suitable materials include those described above for use in the absorbent article 20. In addition, suitable materials may be fluid permeable and at least somewhat temperature-conductive.

In another aspect of the present invention, the structural layer or the additional layer may include a suitable skin adhesive to enhance contact between the thermal grill 110 and the wearer's skin.

In yet another aspect of the present invention, the thermal grill 110 may be positioned on a suspension liner (not shown) to enhance contact between the thermal grill 110 and the wearer's skin. An exemplary suspension liner is shown in co-pending and co-assigned U.S. Patent Application Publication No. 2004/0127880, published on Jul. 1, 2004 by Weber.

The endothermic and exothermic materials are essentially temperature-neutral when resident on the training absorbent article 20. The endothermic and exothermic materials do not have a cooling or warming effect when the training absorbent article 20 is donned by the wearer. It is only upon a urination event/urine insult that endothermic and exothermic materials react and exhibit cooling and warming effects, respectively. Once the warm and cool portions 116, 118 are activated, the thermal grill effect is activated, resulting in the individual, whose skin is in contact with the thermal grill 110, feeling discomfort without physiological damage. Thus, the thermal grill 110 may be activated by liquid provided by the wearer of the training absorbent article 20 in a urination event or urine insult.

In another aspect of the present invention, the warm and cool portions 116, 118 of the thermal grill 110 are formed using Peltier devices configured to alternately form the warm and cool portions 116, 118. Peltier devices are known in the art and create a heat difference from electricity. A current is passed through two dissimilar metals or semiconductors that are connected to each other at two junctions. The current drives a heat transfer from one junction to the other. As a result, one junction becomes the hot side as it increases in temperature while the other junction becomes the cold side as it is reduced in temperature. Positioning Peltier devices with alternating hot and cold sides creates warm and cool portions 116, 118 and therefore a thermal grill 110. In another aspect of the present invention, the Peltier device has a first setting exhibiting a first temperature difference between the warm and cool portions when activated and a second setting exhibiting a second temperature difference between the warm and cool portions when activated. In this aspect, the second temperature difference is greater than the first temperature difference, yielding a more intense, unique sensation with the second setting. The first setting may be used upon a first insult, and the second setting may be used upon a second insult if no action is taken following the first insult.

Because Peltier devices are not themselves switchable by urine insult, a sensing system is also used to detect a urine insult and to turn on the Peltier devices. An example of such a sensing system is described in co-pending and co-assigned U.S. patent application Ser. No. 11/414,032, filed on Apr. 27, 2006 by Allen, et al. and titled "An Array of Wetness Sensing Articles"; which is incorporated herein by reference to the extent it is consistent (i.e., not in conflict) herewith.

In still another aspect of the present invention, the warm and cool portions 116, 118 of the thermal grill 110 are formed using mechanical structures configured to alternately form the warm and cool portions 116, 118. For example, the warm and cool portions 116, 118 may be alternating channels such as tubes or pipes in which reside or through which flow warm and cool fluids, respectively. Warm and cool fluids may be supplied from external sources as is known in the art. Because a mechanical system is not itself switchable by urine insult, a sensing system is also used to detect a urine insult and to turn on the mechanical system. An example of such a sensing system is described in the above-described U.S. patent application Ser. No. 11/414,032.

Figure 2:
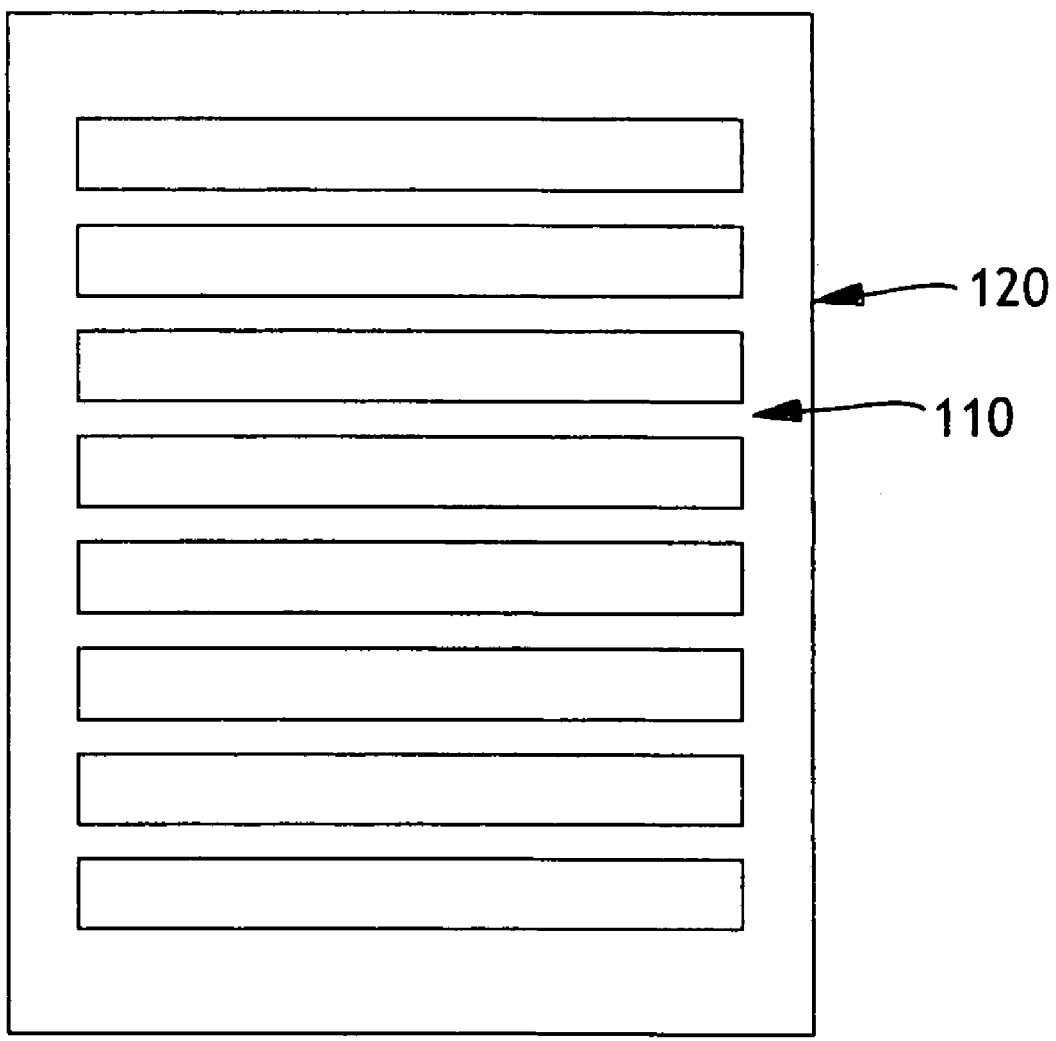
FIG. 2 illustrates a plan view of another aspect of a training article for delivering a unique sensation without causing physiological damage.

In other aspects of the present invention shown in FIG. 2, the thermal grill 110 may be arranged by any of the aspects described herein on a structural layer as a stand-alone garment insert 120 usable with any garment including standard underwear and absorbent articles. In these aspects, the thermal grill 110 is arranged as described above with the exception that the remainder of an absorbent article other than a structural layer is not present. In addition, the structural layer may be coupled to a backing layer or layers by any suitable means. Also, the garment insert 120 may include means to attach the garment insert 120 to a garment such as adhesive, hook, loop, snaps, elastic, folds, buttons, pins, any other suitable attachment means, or a combination of these.

In the garment insert aspect of the present invention, the wearer of a garment or the caregiver of the wearer positions the garment insert 120 including the thermal grill 110 within the wearer's garment. The article then performs as described above, reacting to a urine insult in the manner described.

The sense of discomfort created in the wearer upon activation of the thermal grill 110 is a very effective consequential training stimulus to alert the wearer to avoid wetting the training absorbent article 20.

So that a caregiver may be alerted to an insult event and given the opportunity to interact with the wearer, other sensing or indication means may be employed. In addition to providing a thermal grill effect to alert the wearer to urination, the training absorbent article 20 may further include one or more other wetness sensing or indication systems to supplement the thermal grill 110. In various aspects of the present invention, the training absorbent article 20 may include additional features such as those disclosed in co-pending and co-assigned U.S. patent application Ser. No. 11/303,283, filed Dec. 15, 2005 by Long, et al. and entitled "Garments With Easy-To-Use Signaling Device"; and U.S. patent application Ser. No. 11/215,937, filed Aug. 31, 2005 by Ales, et al. and entitled "Method of Detecting the Presence of an Insult in an Absorbent Article and Device for Detecting the Same"; which are incorporated herein by reference to the extent they are consistent (i.e., not in conflict) herewith. In another example, the training absorbent article 20 may include a wetness liner such as that described in U.S. Pat. No. 6,658,432 to Underhill et al., which is incorporated herein by reference to the extent it is consistent (i.e., not in conflict) herewith. The training absorbent article 20 may also include other wetness sensing features such as fading ink, appearing ink, a tactile component, or a cooling component.

In various aspects of the present invention, the system 100 may include informational items such as instructions in the use of the product and tips for toilet training, enuresis control, or incontinence control. As used herein, the term "informational item" refers to objects that are provided in addition to training articles, are adapted to communicate information to the user and/or consumer of the training article, and are associated with individual components of the system 100. Examples of informational items include cards, paper, electronic media, printing on the packaging, or other suitable media capable of storing and conveying information.

In various aspects, the informational items associated with the system components may be adapted to appeal to the specific category of user and/or purchaser to which the training article is adapted. The informational items may be adapted, for example, by providing information likely to be of interest to a given category of user and/or purchaser.

For example, a training article may be adapted for use by a caregiver for toilet training purposes. An informational item may be associated with the training article that is adapted to interest caregivers. For example, the informational item may be a card containing information or instructions about children's health and hygiene, such as sleep habits, thumb sucking, teething, skin health, toilet training, questions to ask a child, jokes, and the like, and combinations thereof. The informational item may additionally or alternatively include addresses for web sites available on the Internet. The web sites may contain information related to issues of interest for caregivers and users of training articles.

The informational item may additionally or alternatively include information describing activities that are suitable for caregivers and users of training articles. The activities may be adapted for a child at a specific age, size, and/or stage of development. For example, the activities may be adapted to promote interaction between the child and the caregiver.

The informational item may additionally or alternatively include information describing the benefits to be derived from using the system 100. This informational item would be part of a promotional plan emphasizing the customizability of the system 100 for the benefit of the consumer, caregiver, and/or user. This informational item would both explain the use of the various components of the system 100 as well as presenting the additional components that may be available and the various combinations that are possible to achieve different goals.

EXAMPLE 1

A thermal grill using materials such as those described above was constructed. Alternating areas of warm and cool portions were established using XYLISORB xylitol 700 Batch E0929, available from Roquette America Inc., as the endothermic material and calcium chloride in the form of DAMPRID moisture controller, available from DampRid, Inc., as the exothermic material, where the calcium chloride was crushed to approximately the same particle size as that of the endothermic material. The endothermic and exothermic materials were sandwiched between two sheets of a perforated film nonwoven material available from Tredegar. Each area of material was approximately 38 mm by 10 mm and contained approximately 1.5 grams of material per area. The areas were separated by approximately 3 mm (in which there was no endothermic or exothermic material). There were 4 areas of each material, again in an alternating arrangement.

The thermal grill was then sprayed with warm water, to simulate a urine insult and to better dissolve the endothermic and exothermic materials. Enough water was used to obtain a noticeable temperature change in the endothermic and exothermic materials. The warm and cool portions were tested using a single finger tip to make sure the endothermic and exothermic chemistries were working as desired and expected.

A test subject placed his right forearm on the thermal grill and immediately felt a sensation of "heat" that was much greater than sensation felt on any of the individual warm portions. The subject quickly removed his arm. A second, identical thermal grill was prepared, and a second test subject felt an identical sensation using his hand. Both test subjects reported that the sensation was unpleasant but not long lasting. Neither test subject experienced skin damage or any physical effects.

EXAMPLE 2

A thermal grill using materials such as those described above was constructed. Alternating areas of warm and cool portions were established using XYLISORB xylitol 700 Batch E0929, available from Roquette America Inc., as the endothermic material and magnesium chloride as the exothermic material. The magnesium chloride was crushed to approximately the same particle size as that of the endothermic material and then mixed in a proportion of one part magnesium chloride to three parts Laponite SMF (CP1334) clay, available as sample reference #2093 from Rockwood Additives in Widnes, Cheshire, Great Britain. The endothermic and exothermic materials were sandwiched between two sheets of a perforated film nonwoven material available from Tredegar. Each area of material was approximately 38 mm by 10 mm and contained approximately 1.5 grams of material per area. The areas were separated by approximately 3 mm (in which there was no endothermic or exothermic material). There were four areas of each material, again in an alternating arrangement.

The thermal grill was then sprayed with warm water, to simulate a urine insult and to better dissolve the endothermic and exothermic materials. Enough water was used to obtain a noticeable temperature change in the endothermic and exothermic materials. The warm and cool portions were tested using a single finger tip to make sure the endothermic and exothermic chemistries were working as desired and expected. The addition of clay to the exothermic material appeared to increase the duration of heating by the exothermic material.

Test subjects in a single-blind manner placed their forearms on the thermal grill and immediately felt a sensation of "heat" that was much greater than sensation felt on any of the individual warm portions. All test subjects reported that the sensation was unpleasant but not long lasting. Test subjects experienced no skin damage or any physical effects.

EXAMPLE 3

A thermal grill using materials such as those described above was constructed. Alternating areas of warm and cool portions were established using warmed and cooled water circulating in copper piping. Quarter-inch copper pipes were arranged in an alternating array of 12 warm and 12 cool pipes. Pipes were an elongated U-shape with one set 1 inch high and 5.5 inches wide with the other set 1 inch high and 7.5 inches wide. The pipes were soldered into 0.75 inch by 0.75 inch steel manifolds to provide common entry and common exit of the water.

Warm water was produced with a Precision Model Number 281 water bath from Precision Scientific, Inc. Cold water was produced with the addition of ice to a beaker of water until a given temperature was produced. The water was pumped with a MASTERFLEX peristaltic pump available from Cole Palmer: Model Number 7550-10 manufactured by the Barnant Company of Barrington, Ill. The pump size used was 7024-21. Temperatures were measured with surface mounted Type K thermocouples read by a DIGI-SENSE Scanning Digital Thermometer Model Number 92800-10 manufactured by the Barnant Company, Barrington, Ill., and adjusted until the thermal grill effect was apparent.

Test subjects placed their forearms on the thermal grill and immediately felt a sensation of "heat" that was much greater than sensation felt on any of the individual warm portions. All test subjects reported that the sensation was unpleasant but not long lasting. Test subjects experienced no skin damage or any physical effects.

While the invention has been described in detail with respect to the specific aspects thereof, it will be appreciated that those skilled in the art, upon attaining an understanding of the foregoing, may readily conceive of alterations to, variations of, and equivalents to these aspects that fall within the spirit and scope of the present invention, which should be assessed accordingly to that of the appended claims.

We claim:

1. An aid for use with a wearer's garment, the aid comprising:
a structural layer having a skin-facing side, wherein the structural layer is adapted to be positioned within the garment such that the skin-facing side is in at least partial skin contact with the wearer; and
a thermal grill disposed on the structural layer.

2. The aid of claim 1, wherein the garment is an absorbent article.

3. The aid of claim 2, wherein the absorbent article is a training pant.

4. The aid of claim 2, wherein the structural layer is one of a bodyside liner, a surge layer, an absorbent layer, and an outer cover.

5. The aid of claim 1, wherein the structural layer is a bodyside liner.

6. The aid of claim 1, wherein the thermal grill includes a cool portion having an endothermic material and a warm portion having an exothermic material.

7. The aid of claim 6, wherein the endothermic material is a carbohydrate.

8. The aid of claim 7, wherein the carbohydrate is xylitol or dextrose.

9. The aid of claim 6, wherein the endothermic material is a salt hydrate.

10. The aid of claim 9, wherein the salt hydrate is sodium acetate, sodium carbonate, sodium sulfate, sodium thiosulfate, or sodium phosphate.

11. The aid of claim 6, wherein the endothermic material is an anhydrous salt.

12. The aid of claim 11, wherein the anhydrous salt is ammonium nitrate, potassium nitrate, ammonium chloride, potassium chloride, sodium bromide, magnesium sulfate, or sodium nitrate.

13. The aid of claim 6, wherein the endothermic material is urea.

14. The aid of claim 6, wherein the endothermic material is a ketal.

15. The aid of claim 6, wherein the exothermic material is a metal-halogen compound.

16. The aid of claim 15, wherein the metal-halogen compound is aluminum chloride, magnesium chloride, calcium chloride, or manganese iodide.

17. The aid of claim 6, wherein the exothermic material is a salt.

18. The aid of claim 17, wherein the salt is aluminum sulfate or potassium aluminum sulfate.

19. The aid of claim 6, wherein the exothermic material is a metal hydroxide.

20. The aid of claim 19, wherein the metal hydroxide is calcium oxide, barium oxide, or phosphorous pentoxide.

21. The aid of claim 6, wherein the exothermic material is a polymer.

22. The aid of claim 6, wherein the exothermic material is urine.

23. The aid of claim 6, wherein one of the warm and cool portions includes a filler material.

24. The aid of claim 1, further comprising a wetness indicating system.

25. The aid of claim 1, wherein the thermal grill is an alternating pattern of cool portions and warm portions.

26. The aid of claim 1, wherein the thermal grill has a cool portion including a cold side of a Peltier device and a warm portion including a hot side of a Peltier device.

27. The aid of claim 26, the Peltier device having
a first setting exhibiting a first temperature difference between the warm and cool portions when activated; and
a second setting exhibiting a second temperature difference between the warm and cool portions when activated; wherein the second temperature difference is greater than the first temperature difference.

28. The aid of claim 1, wherein the thermal grill has cool and warm portions each including a fluid-accommodating channel.

29. The aid of claim 1, wherein the thermal grill includes a covering layer.

30. An absorbent article for delivering a unique sensation without causing physiological damage, the article comprising:
a bodyside liner;
a plurality of warm portions disposed on the bodyside liner; and
a plurality of cool portions disposed on the bodyside liner, wherein the warm portions and cool portions are disposed in an alternating pattern.

31. The article of claim 30, wherein the alternating pattern is stripes.

32. The article of claim 30, wherein the alternating pattern is a checkerboard pattern.

33. The article of claim 30, wherein the alternating pattern is a non-geometric design.

34. An absorbent article for delivering a unique sensation without causing physiological damage, the article comprising:
a structural layer, wherein the structural layer is one of a bodyside liner, a surge layer, an absorbent layer, and an outer cover; and
a thermal grill disposed on the structural layer.

35. The article of claim 34, wherein the structural layer is the bodyside liner.

36. A method for training comprising:
supplying a training article including a structural layer and a thermal grill disposed on the structural layer; and
providing an informational item associated with the training.

37. A system of aid products, the system comprising:
a first structural layer having a first thermal grill with first warm and cool portions, the first thermal grill exhibiting a first temperature difference between the first warm and cool portions when activated; and
a second structural layer having a second thermal grill with second warm and cool portions, the second thermal grill exhibiting a second temperature difference between the second warm and cool portions when activated; wherein the second temperature difference is greater than the first temperature difference.

38. The system of claim 37, wherein the first structural layer is in a first product, and wherein the second structural layer is in a second product.

39. The system of claim 38, wherein the first and second products are both absorbent articles or both garment inserts.

40. The system of claim 38, wherein one of the first and second products is an absorbent article, and the other of the first and second products is a garment insert.

41. The system of claim 37, wherein the first and second structural layers are the same layer in one product.

42. A method for providing a system of aid products, the method comprising:
providing a first product having a first thermal grill exhibiting a first level of discomfort when activated; and
providing a second product having a second thermal grill exhibiting a second level of discomfort when activated, wherein the second level of discomfort is greater than the first level of discomfort.

43. The method of claim 42, wherein each thermal grill has a warm and a cool portion, and wherein the level of discomfort for that thermal grill is indicated by a temperature difference between the warm and cool portions of that thermal grill.

* * * * *